(12) United States Patent
Bartsch et al.

(10) Patent No.: US 7,022,866 B2
(45) Date of Patent: Apr. 4, 2006

(54) PHOSPHONITES

(75) Inventors: Michael Bartsch, Neustadt (DE);
Robert Baumann, Mannheim (DE);
Dagmar Pascale Kunsmann-Keitel,
Limburgerhof (DE); Gerd Haderlein,
Darmstadt (DE); Tim Jungkamp,
Dossenheim (DE); Marco Altmayer,
Mannheim (DE); Wolfgang Siegel,
Limburgerhof (DE); Ferenc Molnar,
Speyer (DE)

(73) Assignee: BASF Aktiengesellschaft,
Ludwigshafen (DE)

( * ) Notice: Subject to any disclaimer, the term of this patent is extended or adjusted under 35 U.S.C. 154(b) by 135 days.

(21) Appl. No.: 10/491,964

(22) PCT Filed: Oct. 1, 2002

(86) PCT No.: PCT/EP02/10985

§ 371 (c)(1),
(2), (4) Date: Apr. 8, 2004

(87) PCT Pub. No.: WO03/033141

PCT Pub. Date: Apr. 24, 2003

(65) Prior Publication Data
US 2004/0235648 A1 Nov. 25, 2004

(30) Foreign Application Priority Data
Oct. 12, 2001 (DE) .............................. 101 50 285

(51) Int. Cl.
*C07F 15/04* (2006.01)
*C07F 9/02* (2006.01)
*B01J 31/00* (2006.01)
*C07C 253/00* (2006.01)

(52) U.S. Cl. .................. 556/18; 556/19; 502/162; 568/17; 558/335; 558/355

(58) Field of Classification Search .............. 556/18, 556/19; 502/162; 468/17, 335, 355
See application file for complete search history.

(56) References Cited

U.S. PATENT DOCUMENTS

| | | | |
|---|---|---|---|
| 3,496,217 A | 2/1970 | Drinkard, Jr. ............ | 260/465.8 |
| 3,496,218 A | 2/1970 | Drinkard, Jr. ............ | 260/465.8 |
| 3,766,237 A | 10/1973 | Chia et al. ............... | 260/465.3 |
| 3,850,973 A | 11/1974 | Seidel et al. ............. | 260/464 |
| 3,903,120 A | 9/1975 | Shook et al. ............ | 260/439 R |
| 4,493,906 A | 1/1985 | Couvillion ............... | 502/346 |
| 4,587,369 A | 5/1986 | Cosyns et al. ............ | 585/259 |
| 4,704,492 A | 11/1987 | Nemet-Mavrodin ....... | 585/259 |

(Continued)

FOREIGN PATENT DOCUMENTS

GB 1 377 228 12/1974

(Continued)

OTHER PUBLICATIONS

"Applied Homogeneous Catalysis with Organometalic Compounds", BD. 1, VCH Weinheim, S. 479.

(Continued)

*Primary Examiner*—Porfirio Nazario-Gonzalez
(74) *Attorney, Agent, or Firm*—Novak Druce & Quigg LLP; Jason D. Voight

(57) ABSTRACT

Phosphonites I of the formula 1 or 2

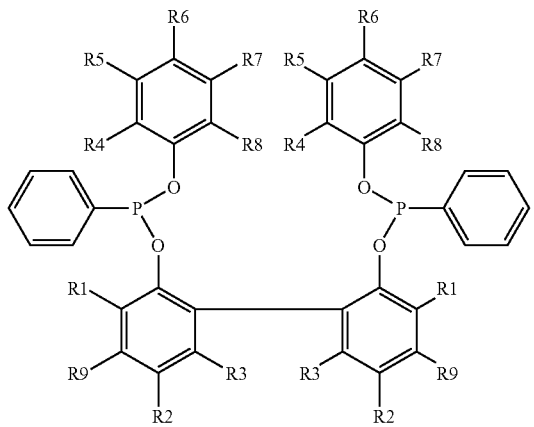

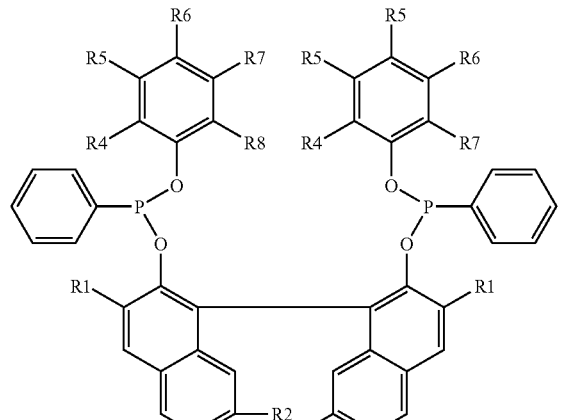

where
R1, R2 are each, independently of one another, hydrogen, an alkyl or alkylene group having from 1 to 8 carbon atoms or an alkoxy group having from 1 to 8 carbon atoms, with the proviso that R1 and R2 are not simultaneously H,
R3 is H or methyl,
R4 is t-butyl,
R5, R6, R7, R8, R9 are each, independently of one another, H or an alkyl or alkylene group having from 1 to 8 carbon atoms.

12 Claims, No Drawings

U.S. PATENT DOCUMENTS

| | | | |
|---|---|---|---|
| 4,774,353 A | 9/1988 | Hall et al. | 558/335 |
| 4,874,884 A | 10/1989 | McKinney et al. | 558/338 |
| 5,523,453 A | 6/1996 | Breikss | 558/338 |
| 5,693,843 A | 12/1997 | Breikss et al. | 558/338 |
| 5,981,772 A | 11/1999 | Foo et al. | 549/349 |
| 6,127,567 A | 10/2000 | Garner et al. | 558/338 |
| 6,521,778 B1 * | 2/2003 | Fischer et al. | 558/338 |

FOREIGN PATENT DOCUMENTS

| | | |
|---|---|---|
| GB | 6171966 | 1/2001 |
| WO | 99/64155 | 12/1999 |
| WO | 00/13983 | 3/2000 |

OTHER PUBLICATIONS

Ullmanns Enzyklopedie der technischem Chemie, Bd. 1,3. Aufl. 1951, S. 743.

Ullmanns Enzyklopedie der technischem Chemie, Bd. 1,3. Aufl. 1951, S. 769.

* cited by examiner

PHOSPHONITES

The present invention relates to novel phosphonites, in particular chelating phosphonites, methods of preparing them, their use as ligands in transition metal complexes, novel transition metal complexes, a process for preparing the complexes, their use as catalyst and processes carried out in the presence of such transition metal complexes as catalysts.

Chelating phosphonites, nickel complexes containing such phosphonites as ligands and the use of such complexes as catalysts are known.

WO 99/13983 and WO 99/64155 describe a process for the hydrocyanation of unsaturated organic compounds and the isomerization of nitriles in the presence of nickel(0) complexes containing chelating phosphonites as ligands. The chelating phosphonites described do have a good stability under the corresponding reaction conditions. It would be desirable to improve the stability of the chelating phosphonite ligands to increase the operating life of the catalyst. Furthermore, an improvement in the selectivity of the catalyst, for example to 3-pentenenitrile in the hydrocyanation of butadiene or to adiponitrile in the hydrocyanation of 3-pentenenitrile, and an improvement in the space-time yield are desirable.

It is an object of the present invention to provide phosphonites which are suitable as chelating phosphonites and display high stability, high reactivity and high selectivity when used as catalysts in the hydrocyanation of unsaturated organic compounds. We have found that this object is achieved by phosphonites I of the formula 1 or 2 formula 1

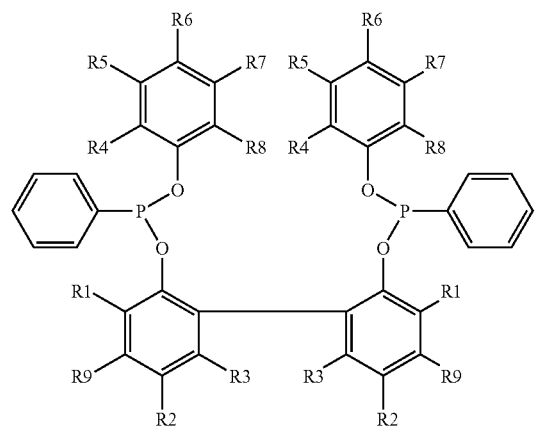

formula 2

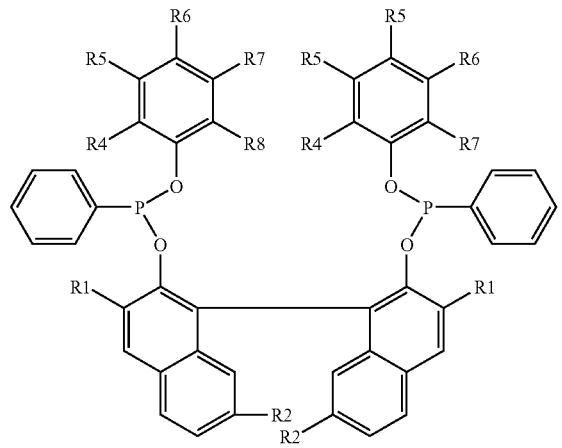

where

R1, R2 are each, independently of one another, hydrogen, an alkyl or alkylene group having from 1 to 8 carbon atoms or an alkoxy group having from 1 to 8 carbon atoms, with the proviso that R1 and R2 are not simultaneously H, R3 is H or methyl, R4 is t-butyl, R5, R6, R7, R8, R9 are each, independently of one another, H or an alkyl or alkylene group having from 1 to 8 carbon atoms.

The present invention also provides methods of preparing them, provides for their use as ligands in transition metal complexes, provides novel transition metal complexes and processes for preparing them, provides for their use as catalyst and provides processes carried out in the presence of such transition metal complexes as catalyst.

According to the present invention, the radicals R1 and R2 are each, independently of one another, hydrogen, an alkyl or alkylene group having from 1 to 8 carbon atoms, or an alkoxy group having from 1 to 8 carbon atoms, with the proviso that R1 and R2 are not simultaneously H.

As alkyl or alkylene group having from 1 to 8 carbon atoms, preference is given to an alkyl group having from 1 to 8 carbon atoms, in particular from 1 to 4 carbon atoms, advantageously selected from the group consisting of methyl, ethyl, n-propyl, i-propyl, n-butyl, s-butyl, i-butyl and t-butyl, in particular from the group consisting of methyl, ethyl, n-propyl, i-propyl and t-butyl.

As alkoxy group having from 1 to 8 carbon atoms, preference is given to an alkoxy group having from 1 to 4 carbon atoms, advantageously selected from the group consisting of methoxy, ethoxy, n-propoxy, i-propoxy, n-butoxy, s-butoxy, i-butoxy and t-butoxy, in particular methoxy.

In the case of a phosphonite I of the formula 1, an advantageous, preferred embodiment provides for R1 and R2 each to be, independently of one another, an alkyl group which has from 1 to 4 carbon atoms and is preferably selected from the group consisting of methyl, ethyl, n-propyl, i-propyl, n-butyl, s-butyl, i-butyl and t-butyl, in particular from the group consisting of methyl, ethyl, n-propyl, i-propyl and t-butyl.

In the case of a phosphonite I of the formula 2, an advantageous, preferred embodiment provides for R1 and R2 each to be, independently of one another, hydrogen, an alkyl group which has from 1 to 4 carbon atoms and is preferably selected from the group consisting of methyl, ethyl, n-propyl, i-propyl, n-butyl, s-butyl, i-butyl and t-butyl, in particular from the group consisting of methyl, ethyl, n-propyl, i-propyl and t-butyl, or an alkoxy group which has from 1 to 4 carbon atoms and is advantageously selected from the group consisting of methoxy, ethoxy, n-propoxy, i-propoxy, n-butoxy, s-butoxy, i-butoxy and t-butoxy, in particular methoxy. In a particularly preferred embodiment, R1 can be an alkyl group which has from 1 to 4 carbon atoms and is preferably selected from the group consisting of methyl, ethyl, n-propyl, i-propyl, n-butyl, s-butyl, i-butyl and t-butyl, in particular from the group consisting of methyl, ethyl, n-propyl, i-propyl and t-butyl, particularly preferably methyl, and R2 can be hydrogen or an alkoxy group which has from 1 to 4 carbon atoms and is advantageously selected from the group consisting of methoxy, ethoxy, n-propoxy, i-propoxy, n-butoxy, s-butoxy, i-butoxy and t-butoxy, in particular methoxy.

According to the present invention, R3 is H or a methyl group.

According to the present invention, R4 is a t-butyl group.

According to the present invention, the radicals R5, R6, R7, R8 and R9 are each, independently of one another, hydrogen or an alkyl or alkylene group having from 1 to 8 carbon atoms.

Particularly preferred phosphonites I of the formula 1 are those in which the radicals R1, R2, R3, R4, R5, R6, R7, R8 and R9 are as shown in Table 1 below.

TABLE 1

| No. | R1 | R2 | R3 | R4 | R5 | R6 | R7 | R8 | R9 |
|---|---|---|---|---|---|---|---|---|---|
| 1 | Me | Me | H | t-Bu | H | H | H | H | H |
| 2 | Et | Et | H | t-Bu | H | H | H | H | H |
| 3 | n-Pr | n-Pr | H | t-Bu | H | H | H | H | H |
| 4 | t-Bu | t-Bu | H | t-Bu | H | H | H | H | H |
| 5 | Et | Me | H | t-Bu | H | H | H | H | H |
| 6 | n-Pr | Me | H | t-Bu | H | H | H | H | H |
| 7 | t-Bu | Me | H | t-Bu | H | H | H | H | H |
| 8 | Me | Me | H | t-Bu | H | H | H | H | Me |
| 9 | t-Bu | Me | Me | t-Bu | H | H | H | H | H |
| 10 | Me | Me | H | t-Bu | H | t-Bu | H | H | H |
| 11 | Et | Et | H | t-Bu | H | t-Bu | H | H | H |
| 12 | n-Pr | n-Pr | H | t-Bu | H | t-Bu | H | H | H |
| 13 | t-Bu | t-Bu | H | t-Bu | H | t-Bu | H | H | H |
| 14 | Et | Me | H | t-Bu | H | t-Bu | H | H | H |
| 15 | n-Pr | Me | H | t-Bu | H | t-Bu | H | H | H |
| 16 | t-Bu | Me | H | t-Bu | H | t-Bu | H | H | H |
| 17 | Me | Me | H | t-Bu | H | t-Bu | H | H | Me |
| 18 | t-Bu | Me | Me | t-Bu | H | t-Bu | H | H | H |
| 19 | Me | Me | H | t-Bu | H | Me | H | H | H |
| 20 | Et | Et | H | t-Bu | H | Me | H | H | H |
| 21 | n-Pr | n-Pr | H | t-Bu | H | Me | H | H | H |
| 22 | t-Bu | t-Bu | H | t-Bu | H | Me | H | H | H |
| 23 | Et | Me | H | t-Bu | H | Me | H | H | H |
| 24 | n-Pr | Me | H | t-Bu | H | Me | H | H | H |
| 25 | t-Bu | Me | H | t-Bu | H | Me | H | H | H |
| 26 | Me | Me | H | t-Bu | H | Me | H | H | Me |
| 27 | t-Bu | Me | Me | t-Bu | H | Me | H | H | H |
| 28 | Me | Me | H | t-Bu | H | H | Me | H | H |
| 29 | Et | Et | H | t-Bu | H | H | Me | H | H |
| 30 | n-Pr | n-Pr | H | t-Bu | H | H | Me | H | H |
| 31 | t-Bu | t-Bu | H | t-Bu | H | H | Me | H | H |
| 32 | Et | Me | H | t-Bu | H | H | Me | H | H |
| 33 | n-Pr | Me | H | t-Bu | H | H | Me | H | H |
| 34 | t-Bu | Me | H | t-Bu | H | H | Me | H | H |
| 35 | Me | Me | H | t-Bu | H | H | Me | H | Me |
| 36 | t-Bu | Me | Me | t-Bu | H | H | Me | H | H |
| 37 | Me | Me | H | t-Bu | H | H | H | Me | H |
| 38 | Et | Et | H | t-Bu | H | H | H | Me | H |
| 39 | n-Pr | n-Pr | H | t-Bu | H | H | H | Me | H |
| 40 | t-Bu | t-Bu | H | t-Bu | H | H | H | Me | H |
| 41 | Et | Me | H | t-Bu | H | H | H | Me | H |
| 42 | n-Pr | Me | H | t-Bu | H | H | H | Me | H |
| 43 | t-Bu | Me | H | t-Bu | H | H | H | Me | H |
| 44 | Me | Me | H | t-Bu | H | H | H | Me | Me |
| 45 | t-Bu | Me | Me | t-Bu | H | H | H | Me | H |
| 46 | Me | Me | H | t-Bu | H | Me | H | Me | H |
| 47 | Et | Et | H | t-Bu | H | Me | H | Me | H |
| 48 | n-Pr | n-Pr | H | t-Bu | H | Me | H | Me | H |
| 49 | t-Bu | t-Bu | H | t-Bu | H | Me | H | Me | H |
| 50 | Et | Me | H | t-Bu | H | Me | H | Me | H |
| 51 | n-Pr | Me | H | t-Bu | H | Me | H | Me | H |
| 52 | t-Bu | Me | H | t-Bu | H | Me | H | Me | H |
| 53 | Me | Me | H | t-Bu | H | Me | H | Me | Me |
| 54 | t-Bu | Me | Me | t-Bu | H | Me | H | Me | H |

Particularly preferred phosphonites I of the formula 2 are those in which the radicals R1, R2, R4, R5, R6, R7 and R8 are as shown in Table 1 below.

TABLE 2

| No. | R1 | R2 | R4 | R5 | R6 | R7 | R8 |
|---|---|---|---|---|---|---|---|
| 55 | Me | H | t-Bu | H | H | H | H |
| 56 | Me | H | t-Bu | H | t-Bu | H | H |
| 57 | Me | H | t-Bu | H | Me | H | H |
| 58 | Me | H | t-Bu | H | H | Me | H |
| 59 | Me | H | t-Bu | H | H | H | Me |
| 60 | Me | H | t-Bu | H | Me | H | Me |
| 61 | Me | OMe | t-Bu | H | H | H | H |
| 62 | Me | OMe | t-Bu | H | t-Bu | H | H |
| 63 | Me | OMe | t-Bu | H | Me | H | H |
| 64 | Me | OMe | t-Bu | H | H | Me | H |
| 65 | Me | OMe | t-Bu | H | H | H | Me |
| 66 | Me | OMe | t-Bu | H | Me | H | Me |

In Table 1 and Table 2, the abbreviations have the following meanings:

| | |
|---|---|
| H: | hydrogen |
| Me: | methyl |
| Et: | ethyl |
| n-Pr: | n-propyl |
| t-Bu: | t-butyl |
| OMe: | methoxy |

The preparation of phosphonite I can be carried out using a method analogous to that described in WO 99/64155 for the phosphonite ligands of the formula 1 described there by firstly reacting a phenylphosphorus(III) dihalide, preferably phenylphosphorus(III) dichloride, with a phenol bearing the radicals R4, R5, R6, R7 and R8 to eliminate hydrogen halide and give a phenyl(R4, R5, R6, R7, R8-phenoxy)phosphorus(III) halide. If desired, this reaction product can be isolated and/or purified by known methods, e.g. by distillation, before being reacted further. The phenyl(R4, R5, R6, R7, R8-phenoxy)phosphorus(III) halide can then be reacted with a 2,2'-bisphenol bearing the radicals R1, R2, R3 and R9 in the case of formula 1 or a 2,2'-bisnaphthol bearing the radicals R1 and R2 to eliminate hydrogen halide and give a phosphonite I.

Both reactions can advantageously be carried out at from about to 40 to about 200° C. Both reactions can be carried out in the presence of a base such as an aliphatic amine, for example diethylamine, dipropylamine, dibutylamine, trimethylamine, triethylamine or tripropylamine, or pyridine, preferably triethylamine or pyridine. Preference is given to a purely thermal elimination of hydrogen halide in the first reaction step.

The preparation of the phosphonites I is advantageously carried out without use of organomagnesium or organolithium compounds. The simple reaction sequence makes it possible to prepare a wide range of phosphonites I. The preparation can thus be carried out efficiently and economically from readily available starting materials.

The phosphonites I can be used as ligands in transition metal complexes.

Transition metals which can advantageously be used are the metals of transition groups I, II and VI to VIII of the Periodic Table, preferably transition group VIII of the Period Table, particularly preferably iron, cobalt and nickel, in particular nickel.

If nickel is used, it can be present in various oxidation states such as 0, +1, +2, +3. Preference is given to nickel(0) and nickel(+2), in particular nickel(0).

To prepare the transition metal complexes, a chemical compound of a transition metal or preferably a transition metal can be reacted with a phosphonite I, with the phosphonite I used being able to be either a single phosphonite I or a mixture of a plurality of phosphonites I.

Prior to the reaction, the transition metal can be obtained from suitable chemical compounds, e.g. salts such as chlorides, for example by reduction with base metals such as zinc.

If a transition metal compound is used for preparing the transition metal complexes, advantageous compounds are salts such as chlorides, bromides, acetylacetonates, sulfates, nitrates, for example nickel(2) chloride, or Ni(0) complexes such as bis(1,5-cyclooctadiene)Ni(0).

After the reaction of the transition metal compound or the transition metal with a phosphonite I, the oxidation state of the transition metal in the complex can be altered by means of suitable oxidizing or reducing agents, for example base metals such as zinc or hydrogen in chemically bound form, e.g. sodium borohydride, or in molecular form, or electrochemically.

In a particularly preferred embodiment, a complex of Ni(0) with organic monophosphine, monophosphonite, monophosphonite or monophosphite ligands can be reacted with a phosphonite I using a method based on that described in the German patent application 10136488.1.

In the transition metal complexes, the molar ratio of transition metal to phosphonite I can be in the range from 1 to 6, preferably from 2 to 5, in particular 2, 3 or 4. The transition metal complexes can be free of ligands other than the phosphonites I.

The transition metal complexes may further comprise other ligands in addition to the phosphonites I, for example nitriles such as acetonitrile, adiponitrile, 3-pentenenitrile, 4-pentenenitrile, 2-methyl-3-butenenitrile, olefins such as butadiene or phosphorus compounds such as organic monophosphines, monophosphonites, monophosphonites or monophosphites.

The preparation of such transition metal complexes can be carried out by methods analogous to those described in the literature, for example in DE-A-2 237 703, U.S. Pat. Nos. 3,850,973, 3,766,237 or 3,903,120, for preparing transition metal complexes containing tri-o-tolyl phosphite, tri-m-tolyl phosphite or tri-p-tolyl phosphite ligands by replacing these phosphites partly or completely by the phosphonites I of the present invention.

The transition metal complexes of the present invention can be used as catalysts, in particular as homogeneous catalysts.

It has been found to be particularly advantageous to use the transition metal complexes of the present invention as catalysts in the addition of hydrocyanic acid onto olefinic double bonds, in particular double bonds which are conjugated with a further olefinic double bond, for example onto a double bond of butadiene to give a mixture comprising 2-methyl-3-butenenitrile and 3-pentenenitrile. It is equally advantageous to use the transition metal complexes of the invention as catalysts in the addition of hydrocyanic acid onto olefinic double bond which are not conjugated with a further olefinic double bond, for example onto the double bond of 3-pentenenitrile or 4-pentenenitrile or mixtures thereof, preferably 3-pentenenitrile, to give adiponitrile, or onto 3-pentenoic esters or 4-pentenoic esters or mixtures thereof, preferably 3-pentenoic esters, to give 5-cyanovaleric esters.

It has likewise been found to be particularly advantageous to use the transition metal complexes of the present invention as catalysts in the isomerization of organic nitrites, in particular ones in which the nitrile group is not conjugated with an olefinic double bond, for example the isomerization of 2-methyl-3-butenenitrile to give 3-pentenenitrile. It is equally advantageous to use the transition metal complexes of the present invention as catalysts in the isomerization of organic nitrites in which the nitrile group is conjugated with an olefinic double bond.

Processes for the addition of hydrocyanic acid onto an olefinic double bond or for the isomerization of organic nitriles can be carried out in a manner analogous to that described, for example, in WO 99/13983 or WO 99/64155, by partly or completely replacing the phosphonites described there by the phosphonites I of the present invention.

The invention also provides a process for preparing mixtures of monoolefinic $C_5$-mononitriles having nonconjugated C=C and C=N bonds by hydrocyanation of a 1,3-butadiene-containing hydrocarbon mixture in the presence of at least one of the above described systems according to the present invention as catalyst.

The preparation of monoolefinic $C_5$-mononitriles by the process of the present invention is preferably carried out using a hydrocarbon mixture having a 1,3-butadiene content of at least 10% by volume, preferably at least 25% by volume, in particular at least 40% by volume.

To prepare mixtures of monoolefinic $C_5$-mononitriles which comprise, for example, 3-pentenenitrile and 2-methyl-3-butenenitrile and are suitable as intermediates for further processing to produce adiponitrile, it is possible to use pure butadiene or 1,3-butadiene-containing hydrocarbon mixtures.

1,3-Butadiene-containing hydrocarbon mixtures are available on an industrial scale. Thus, for example, the processing of petroleum by steam cracking of naphtha produces a hydrocarbon mixture known as $C_4$ fraction which has a high total olefin content, with about 40% being 1,3-butadiene and the remainder being made up of monoolefins and multiply unsaturated hydrocarbons and also alkanes. These streams always contain small proportions of generally up to 5% of alkynes, 1,2-dienes and vinylacetylene.

Pure 1,3-butadiene can be isolated from industrially available hydrocarbon mixtures by, for example, extractive distillation.

$C_4$ fractions are, if desired, substantially freed of alkynes, e.g. propyne or butyne, of 1,2-dienes, e.g. propadiene, and of alkenynes, e.g. vinylacetylene. Otherwise, the products in which a C=C double bond is conjugated with the C=N bond are sometimes obtained. It is known from "Applied Homogeneous Catalysis with Organometalic Compounds", vol. 1, VCH Weinheim, p. 479, that the conjugated 2-pentenenitrile formed in the isomerization of 2-methyl-3-butenenitrile and 3-pentenenitrile acts as a reaction inhibitor for the second addition of hydrogen cyanide to form adiponitrile. It has been found that the abovementioned conjugated nitriles obtained in the hydrocyanation of an unpretreated $C_4$ fraction also act as catalyst poisons for the first reaction step of the preparation of adipic acid, namely the monoaddition of hydrogen cyanide.

For this reason, it may be useful to free the hydrocarbon mixture partly or completely of components which form catalyst poisons in the catalytic hydrocyanation, in particular alkynes, 1,2-dienes and mixtures thereof. To remove these components, the $C_4$ fraction is subjected to a catalytic partial hydrogenation before the addition of hydrogen cyanide. This partial hydrogenation is carried out in the presence of a hydrogenation catalyst which is capable of selectively hydrogenating alkynes and 1,2-dienes in the presence of other dienes and monoolefins.

Suitable heterogeneous catalyst systems generally comprise a transition metal compound on an inert support. Suitable inorganic supports are the customary oxides, in particular silicon and aluminum oxides, aluminosilicates, zeolites, carbides, nitrides, etc., and mixtures thereof. Preference is given to using $Al_2O_3$, $SiO_2$ and mixtures thereof as supports. In particular, the heterogeneous catalysts used are those described in U.S. Pat. Nos. 4,587,369; 4,704,492 and 4,493,906, which are hereby fully incorporated by reference. Further suitable catalyst systems based on Cu are marketed by Dow Chemical as KLP catalyst.

The addition reaction of hydrogen cyanide with 1,3-butadiene or a 1,3-butadiene-containing hydrocarbon mixture, e.g. a pretreated, partially hydrogenated $C_4$ fraction, can be carried out continuously, semicontinuously or batchwise.

In a useful variant of the process of the present invention, the addition reaction of the hydrogen cyanide is carried out continuously. Suitable reactors for a continuous reaction are known to those skilled in the art and are described, for example, in Ullmanns Enzyklopädie der technischen Chemie, vol. 1, 3rd edition, 1951, p. 743 ff. The continuous variant of the process of the present invention is preferably carried out using a cascade of stirred vessels or a tube reactor.

In a preferred variant of the process of the present invention, the addition reaction of hydrogen cyanide with 1,3-butadiene or a 1,3-butadiene-containing hydrocarbon mixture is carried out semicontinuously.

The semicontinuous process comprises
a) charging a reactor with the hydrocarbon mixture, if desired part of the hydrogen cyanide and a hydrocyanation catalyst according to the present invention, if desired produced in situ, and, if desired, a solvent,
b) reacting the mixture at elevated temperature and superatmospheric pressure, with hydrogen cyanide being fed in at the rate at which it is consumed,
c) completing the conversion by a period of after-reaction and subsequently working up the mixture.

Suitable pressure-rated reactors are known to those skilled in the art and are described, for example, in Ullmanns Enzyklopädie der technischen Chemie, vol. 1, 3rd edition, 1951, p. 769 ff. In general, the process of the present invention is carried out using an autoclave which may, if desired, be provided with a stirrer and an internal lining. For the above steps, the following procedures/conditions are preferred:

Step a):

The pressure-rated reactor is charged with the partially hydrogenated $C_4$ fraction or butadiene, hydrogen cyanide, a hydrocyanation catalyst and, if desired, a solvent prior to commencement of the reaction. Suitable solvents are those mentioned above for the preparation of the catalysts of the present invention, preferably aromatic hydrocarbons such as toluene and xylene, or tetrahydrofuran.

Step b):

The mixture is generally reacted at elevated temperature and superatmospheric pressure. The reaction temperature is generally in a range from about 0 to 200° C., preferably from about 50 to 150° C. The pressure is generally in a range from about 1 to 200 bar, preferably from about 1 to 100 bar, in particular from 1 to 50 bar, particularly preferably from 1 to 20 bar. During the reaction, hydrogen cyanide is fed in at a rate corresponding to that at which it is consumed, with the pressure in the autoclave remaining essentially constant. The reaction time is from about 30 minutes to 5 hours.

Step c):

To complete the conversion, the reaction time can be followed by an after-reaction time of up to about 5 hours, preferably from about 1 hour to 3.5 hours, during which no more hydrogen cyanide is fed into the autoclave. During this time, the temperature is kept essentially constant at the reaction temperature set during the addition of hydrogen cyanide. Work-up is carried out by customary methods and comprises separating off the unreacted 1,3-butadiene and the unreacted hydrogen cyanide, e.g. by washing or extraction, and fractionally distilling the remaining reaction mixture to separate off the product of value and recover the still active catalyst.

In a further useful variant of the process of the present invention, the addition reaction of the hydrogen cyanide with the 1,3-butadiene-containing hydrocarbon mixture is carried out batchwise. Here, essentially the same reaction conditions as described for the semicontinuous process are maintained, but no additional hydrogen cyanide is fed in step b). All of the hydrogen cyanide is included in the initial charge.

In general, the preparation of adiponitrile from a butadiene-containing mixture by addition of 2 molar equivalents of hydrogen cyanide can be divided into three steps:

1. Preparation of mixtures of $C_5$-monoolefins having a nitrile function.
2. Isomerization of the 2-methyl-3-butenenitrile present in these mixtures to form 3-pentenenitrile and isomerization of the 3-pentenenitrile formed in this way and the 3-pentenenitrile already present in the mixtures from step 1 to form various n-pentenenitriles. A very high proportion of 3-pentenenitrile or 4-pentenenitrile and a very small proportion of conjugated 2-pentenenitrile and 2-methyl-2-butenenitrile, which may act as catalyst poisons, should be formed.
3. Preparation of adiponitrile by addition of hydrogen cyanide onto the 4-pentenenitrile which has previously been formed in situ by isomerization of the 3-pentenenitrile formed in step 2. By-products formed are, for example, 2-methylglutaronitrile from the Markovnikov addition of hydrogen cyanide onto 4-pentenenitrile or the anti-Markovnikov addition of hydrogen cyanide onto 3-pentenenitrile and ethyl succinonitrile from the Markovnikov addition of hydrogen cyanide onto 3-pentenenitrile.

The novel catalysts based on phosphonite ligands can also be used advantageously for the structural isomerization and double bond isomerization in step 2 and/or the second addition of hydrogen cyanide in step 3.

Advantageously, the catalysts used according to the present invention not only display a high selectivity to the monoaddition products obtained in the hydrocyanation of 1,3-butadiene-containing hydrocarbon mixtures but they can also be admixed with an excess of hydrogen cyanide without appreciable deposition of inactive nickel(II) compounds, e.g. nickel(II) cyanide, occurring. In contrast to known hydrocyanation catalysts based on uncomplexed phosphine and phosphite ligands, the catalysts comprising a phosphonite I are thus suitable not only for continuous hydrocyanation processes in which an excess of hydrogen cyanide in the reaction mixture can generally be effectively avoided but also for semicontinuous processes and batch processes in which a large excess of hydrogen cyanide is generally present. The catalysts used according to the present invention and the hydrocyanation processes based on them generally display higher catalyst recycle rates and longer catalyst operating times than do known processes. Apart from the economic aspect, this is also a advantageous for ecological reasons since the nickel cyanide formed by reaction of the active catalyst with hydrogen cyanide is highly toxic and has to be worked up or disposed of at high costs.

Apart from the hydrocyanation of 1,3-butadiene-containing hydrocarbon mixtures, the systems of the present invention are generally suitable for all customary hydrocyanation processes. Particular mention may be made of the hydrocyanation of unactivated olefins, e.g. styrene and 3-pentenenitrile.

The addition of hydrocyanic acid onto an olefinic double bond in the presence of a catalyst system according to the present invention, in particular the addition onto butadiene or onto 3-pentenenitrile, 4-pentenenitrile or a mixture of such pentenenitriles or the isomerization of organic nitriles in the presence of a catalyst system according to the present invention, in particular the isomerization of 2-methyl-3-butenenitrile to 3-pentenenitrile, can advantageously be carried out in the presence of one or more Lewis acids as promoters which influence the activity, selectivity or both of the catalyst system of the present invention. Possible promoters are inorganic and organic compounds in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples which may be mentioned are $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(O\text{-}iso\text{-}Pr)_3$, $MnCl_2$, $ScCl_3$, $AlCl_3$, $(C_8H_{17})AlCl_2$, $(C_8H_{17})_2AlCl$, $(iso\text{-}C_4H_9)_2AlCl$, $Ph_2AlCl$, $PhAlCl_2$, $ReCl_5$, $ZrCl_4$, $ZrCl_2$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$, as are generally described, for example in U.S. Pat. No. 6,171,996 B1. Further suitable promoters are described in the patents U.S. Pat. Nos. 3,496,217, 3,496,218 and 4,774,353. These comprise metal salts such as $ZnCl_2$, $CoI_2$ and $SnCl_2$, and organometallic compounds such as $RAlCl_2$, $R_3SnO_3SCF_3$ and $R_3B$, where R is an alkyl group or aryl groups. U.S. Pat. No. 4,874,884 describes the selection of synergistically effective combinations of promoters to increase the catalystic activity of the catalyst system. Preferred promoters include $CdCl_2$, $FeCl_2$, $ZnCl_2$, $B(C_6H_5)_3$ and $(C_6H_5)_3SnZ$, where Z is $CF_3SO_3$, $CH_3C_6H_4SO_3$ or $(C_6H_5)_3BCN$.

The molar ratio of promoter to nickel in the catalyst system can be in the range from 1:16 to 50:1.

A further advantageous embodiment of hydrocyanation and isomerization may be found in U.S. Pat. No. 5,981,772, whose contents are hereby incorporated by reference, with the proviso that a catalyst system according to the present invention or a mixture of such catalyst systems is used in place of the catalyts mentioned in the patent cited.

A further advantageous embodiment of hydrocyanation and isomerization may be found in U.S. Pat. No. 6,127,567, whose contents are hereby incorporated by reference, with the proviso that a catalyst system according to the present invention or a mixture of such catalyst systems is used in place of the catalyts mentioned in the patent cited.

A further advantageous embodiment of hydrocyanation may be found in U.S. Pat. No. 5,693,843, whose contents are hereby incorporated by reference, with the proviso that a catalyst system according to the present invention or a mixture of such catalyst systems is used in place of the catalyts mentioned in the patent cited. A further advantageous embodiment of hydrocyanation may be found in U.S. Pat. No. 5,523,453, whose contents are hereby incorporated by reference, with the proviso that a catalyst system according to the present invention or a mixture of such catalyst systems is used in place of the catalyts mentioned in the patent cited. The invention is illustrated by the following nonlimiting examples.

EXAMPLES

The yields were determined by gas chromatography (column: 30 m Stabil-Wachs, temperature program: 5 minutes isothermal at 50° C., then heating at a rate of 5° C./min to 240° C., gas chromatograph: Hewlett Packard HP 5890)

All examples were carried out under a protective argon atmosphere.

The abbreviation nickel(0)-(m/p-tolyl phosphite) is used for a mixture comprising 2.35% by weight of Ni(0), 19% by weight of 3-pentenenitrile and 78.65% by weight of m/p-tolyl phosphite having an m/p ratio of 2:1.

Chelating ligands used were:

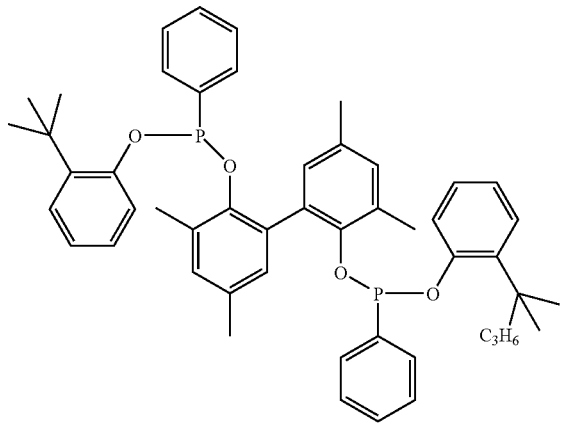

Ligand 1

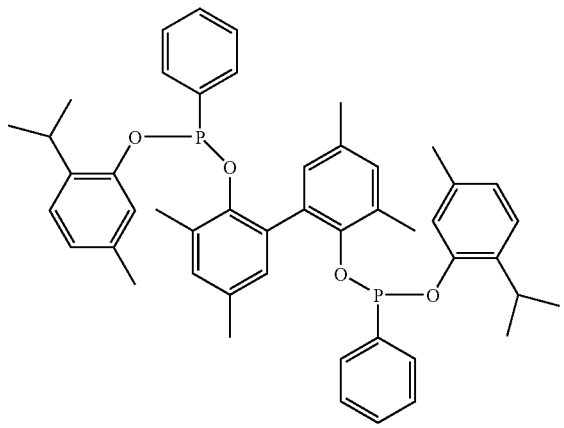

Ligand 2

$Ni(COD)_2$ is used as an abbreviation for bis(1,4-cyclooctadiene)Ni(0), 2M3BN for 2-methyl-3-butenenitrile, t2M2BN for trans-2-methyl-2-butenenitrile, c2M2BN for cis-2-methyl-2-butenenitrile, t2PN for trans-2-pentenenitrile, 4PN for 4-pentenenitrile, t3PN for trans-3-pentenenitrile, c3PN for cis-3-pentenenitrile, MGN for methylglutaronitrile, BD for 1,3-butadiene, HCN for hydrocyanic acid, ADN for adiponitrile and THF for tetrahydrofuran.

Examples 1–3

Isomerization of 2-methyl-3-butenenitrile to form 3-pentenenitrile

Example 1

Comparison (0.5 mmol of Ni(0)

1 equivalent of nickel(0)-(m-/p-tolyl phosphite) was admixed with 465 equivalents of 2M3BN and heated to 115°

C. GC samples were taken from the reaction mixture after 90 minutes and after 180 minutes and analyzed by gas chromatography (GC percent by area). The following results were obtained:

| Time | 2M3BN | t2M2BN | c2M2BN | t2PN | 4PN | c, t-3PN | 3PN/ 2M3BN |
|---|---|---|---|---|---|---|---|
| 90 min | 84.5 | 1.3 | 0.3 | | | 13.0 | 0.15 |
| 180 min | 72.4 | 1.5 | 0.5 | | | 24.4 | 0.34 |

Example 2

According to the Present Invention (0.51 mmol of Ni(0)

1 equivalent of Ni(COD)₂ was admixed with 3 equivalents of ligand 1 and 465 equivalents of 2M3BN, stirred at 25° C. for 1 hour and then heated to 115° C. GC samples were taken from the reaction mixture after 90 minutes and after 180 minutes and analyzed by gas chromatography (GC percent by area). The following results were obtained:

| Time | 2M3BN | t2M2BN | c2M2BN | t2PN | 4PN | t3PN | c3PN | 3PN/2M3BN |
|---|---|---|---|---|---|---|---|---|
| 90 min | 52.54 | 0.05 | 0.13 | 0 | 0.02 | 42.14 | 2.13 | 0.84 |
| 180 min | 11.92 | 0.08 | 0.25 | 0 | 0.13 | 81.05 | 3.18 | 7.07 |

Example 3

According to the Present Invention (0.44 mmol of Ni(0)

1 equivalent of nickel(0)-(m-/p-tolyl phosphite) was admixed with 3 equivalents of ligand 1 and 465 equivalents of 2M3BN, stirred at 25° C. for 12 hours and then heated to 115° C. GC samples were taken from the reaction mixture after 90 minutes and after 180 minutes and analyzed by gas chromatography (GC percent by area). The following results were obtained:

| Time | 2M3BN | t2M2BN | c2M2BN | t2PN | 4PN | t3PN | c3PN | 3PN/2M3BN |
|---|---|---|---|---|---|---|---|---|
| 90 min | 56.99 | 0.16 | 0.27 | 0.01 | 0.03 | 37.39 | 2.58 | 0.71 |
| 180 min | 28.35 | 0.31 | 0.48 | 0.03 | 0.11 | 65.22 | 2.7 | 2.40 |

Examples 4–8

Hydrocyanation of 3-pentenenitrile to form Adiponitrile

Example 4

Comparison (0.6 mmol of Ni(0)

1 equivalent of nickel(0)-(m-/p-tolyl phosphite) was admixed with 365 equivalents of 3PN, stirred at 25° C. for one hour and heated to 70° C. 1 equivalent of ZnCl₂ was added to this mixture and the mixture was stirred for a further 5 minutes. 94 equivalents of HCN/h*Ni in a stream of argon carrier gas were then introduced. GC samples were taken from the reaction mixture after 30 minutes, 60 minutes and 150 minutes and analyzed by gas chromatography (GC percent by weight, internal standard: ethylbenzene). The following results were obtained:

| Time | MGN | ADN | ADN selectivity (%) |
|---|---|---|---|
| 30 min | 3.35 | 10.75 | 76.2 |
| 60 min | 6.87 | 26.39 | 79.3 |
| 150 min | 7.11 | 27.82 | 79.6 |

Example 5

Comparison (0.55 mmol of Ni(0)

1 equivalent of Ni(COD)₂ was admixed with 3 equivalents of ligand 2 and 365 equivalents of 3PN, stirred at 25° C. for one hour and heated to 70° C. 1 equivalent of ZnCl₂ was added to this mixture and the mixture was stirred for a further 5 minutes. 142 equivalents of HCN/h*Ni in a stream of argon carrier gas were then introduced. GC samples were taken from the reaction mixture after 30 minutes and after 60 minutes and analyzed by gas chromatography (GC percent by weight, internal standard: ethylbenzene). The following results were obtained:

| Time | MGN | ADN | ADN selectivity (%) |
|---|---|---|---|
| 30 min | 1.80 | 18.91 | 91.3 |
| 60 min | 2.51 | 32.57 | 92.9 |

-continued

| Time | MGN | ADN | ADN selectivity (%) |
|---|---|---|---|

**The amount of 2PN formed after 60 minutes was 2.80%.

Example 6

Comparison (0.49 mmol of Ni(0)

1 equivalent of Ni(COD)₂ was admixed with 1.2 equivalents of ligand 2, 4 equivalents of m-/p-tolyl phosphite (m:p ratio=2:1) and 365 equivalents of 3PN, stirred at 25° C. for one hour and heated to 70° C. 1 equivalent of ZnCl$_2$ was added to this mixture and the mixture was stirred for a further 5 minutes.

125 equivalents of HCN/h*Ni in a stream of argon carrier gas were then introduced. GC samples were taken from the reaction mixture after 45 minutes and 60 minutes and analyzed by gas chromatography (GC percent by weight, internal standard: ethylbenzene). The following results were obtained:

| Time   | MGN  | ADN   | ADN selectivity (%) |
| ------ | ---- | ----- | ------------------- |
| 45 min | 1.85 | 21.51 | 92.1                |
| 60 min | 2.29 | 27.58 | 92.3                |

The amount of 2PN formed after 60 minutes was 2.41%.

Example 7

According to the Present Invention (0.63 mmol of Ni(0))

1 equivalent of Ni(COD)$_2$ was admixed with 3 equivalents of ligand 1 and 365 equivalents of 3PN, stirred at 25° C. for one hour and heated to 70° C. 1 equivalent of ZnCl$_2$ was added to this mixture and the mixture was stirred for a further 5 minutes. 125 equivalents of HCN/h*Ni in a stream of argon carrier gas were then introduced. GC samples were taken from the reaction mixture after 30 minutes and after 60 minutes and analyzed by gas chromatography (GC percent by weight, internal standard: ethylbenzene). The following results were obtained:

| Time   | MGN  | ADN   | ADN selectivity (%) |
| ------ | ---- | ----- | ------------------- |
| 30 min | 1.28 | 17.11 | 93.1                |
| 60 min | 2.29 | 37.90 | 94.3                |

The amount of 2PN formed after 60 minutes was 1.69%.

Example 8

According to the Present Invention (0.58 mmol of Ni(0))

1 equivalent of nickel(0)-(m-/p-tolyl phosphite) was admixed with 3 equivalents of ligand 1 and 365 equivalents of 3PN, stirred at 25° C. for one hour and heated to 70° C. 1 equivalent of ZnCl$_2$ was added to this mixture and the mixture was stirred for a further 5 minutes. 113 equivalents of HCN/h*Ni in a stream of argon carrier gas were then introduced. GC samples were taken from the reaction mixture after 30 minutes and after 60 minutes and analyzed by gas chromatography (GC percent by weight, internal standard: ethylbenzene). The following results were obtained:

| Time   | MGN  | ADN   | ADN selectivity (%) |
| ------ | ---- | ----- | ------------------- |
| 30 min | 1.1  | 17.52 | 94.1                |
| 60 min | 2.26 | 34.15 | 93.8                |

The amount of 2PN formed after 60 minutes was 1.49%.

Examples 9–13

Hydrocyanation of Butadiene to Form 3-pentenenitrile

Example 9

Comparison (1 mmol of Ni(0))

1 equivalent of nickel(0)-(m-/p-tolyl phosphite) was admixed with 500 equivalents of BD and 420 equivalents of HCN in THF, placed in a glass autoclave at 25° C. and heated to 80° C. The temperature during the reaction (slightly exothermic reaction) was determined by means of an internal thermometer and after 180 minutes the conversion of HCN into 2M3BN and 3PN was determined by gas chromatography (GC percent by weight, internal standard: ethylbenzene). The following results were obtained:

| Time    | Internal temperature |
| ------- | -------------------- |
| 30 min  | 80.3                 |
| 50 min  | 80.5                 |
| 60 min  | 80.4                 |
| 180 min | 80.3                 |

Virtually no temperature increase occurs. This means that the catalyst is not very active.

The conversion of HCN into 2M3BN/3PN was 9.8%. The ratio of 2M3BN/3PN was 1/3.4.

Example 10

Comparison (1 mmol of Ni(0))

1 equivalent of Ni(COD)$_2$ was stirred with 3 equivalents of ligand 2 in THF for 20 minutes. This solution was admixed with 557 equivalents of BD and 433 equivalents of HCN in THF, placed in a glass autoclave at 25° C. and heated to 80° C. The temperature during the reaction (slightly exothermic reaction) was determined by means of an internal thermometer and after 180 minutes the conversion of HCN into 2M3BN and 3PN was determined by gas chromatography (GC percent by weight, internal standard: ethylbenzene). The following results were obtained:

| Time    | Internal temperature |
| ------- | -------------------- |
| 15 min  | 82.2                 |
| 30 min  | 82.1                 |
| 120 min | 81.1                 |

Virtually no temperature increase occurs. This means that the catalyst is not very active.

The conversion of HCN into 2M3BN/3PN was 97.5%. The ratio of 2M3BN/3PN was 1.5/1.

Example 11

Comparison (1 mmol of Ni(0))

1 equivalent of nickel(0)-(m-/p-tolyl phosphite) was stirred with 1.2 equivalents of ligand 2 in THF for 12 hours.

This solution was admixed with 480 equivalents of BD and 400 equivalents of HCN in THF, placed in a glass autoclave at 25° C. and heated to 80° C. The temperature during the reaction (slightly exothermic reaction) was determined by means of an internal thermometer and after 180 minutes the conversion of HCN into 2M3BN and 3PN was determined by gas chromatography (GC percent by weight, internal standard: ethylbenzene). The following results were obtained:

| Time | Internal temperature |
|---|---|
| 30 min | 83.6 |
| 60 min | 84.5 |
| 120 min | 84.4 |
| 180 min | 80.5 |

The conversion of HCN into 2M3BN/3PN was >99%. The ratio of 2M3BN/3PN was 1.35/1.

Example 12

According to the Present Invention (1 mmol of Ni(0)

1 equivalent of Ni(COD)$_2$ was stirred with 3 equivalents of ligand 1 in THF for 20 minutes. This solution was admixed with 480 equivalents of BD and 400 equivalents of HCN in THF, placed in a glass autoclave at 25° C. and heated to 80° C. The temperature during the reaction (slightly exothermic reaction) was determined by means of an internal thermometer and after 180 minutes the conversion of HCN into 2M3BN and 3PN was determined by gas chromatography (GC percent by weight, internal standard: ethylbenzene). The following results were obtained:

| Time | Internal temperature |
|---|---|
| 5 min | 84.8 |
| 10 min | 86.7 |
| 20 min | 88.0 |
| 90 min | 81.2 |

The conversion of HCN into 2M3BN/3PN was >98%. The ratio of 2M3BN/3PN was 1.34/1.

Example 13

According to the Present Invention (1 mmol of Ni(0)

1 equivalent of nickel(0)-(m-/p-tolyl phosphite) was stirred with 1.2 equivalents of ligand 1 in THF for 12 hours. This solution was admixed with 480 equivalents of BD and 400 equivalents of HCN in THF, placed in a glass autoclave at 25° C. and heated to 80° C.

| Time | Internal temperature |
|---|---|
| 5 min | 84.4 |
| 10 min | 87.3 |
| 20 min | 88.7 |
| 90 min | 81.2 |

The conversion of HCN into 2M3BN/3PN was >95%. The ratio of 2M3BN/3PN was 1.3/1.

We claim:

1. A phosphonite I of the formula 1 or 2

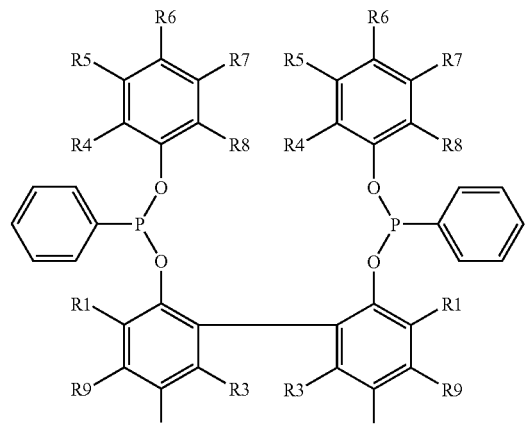

formula 1

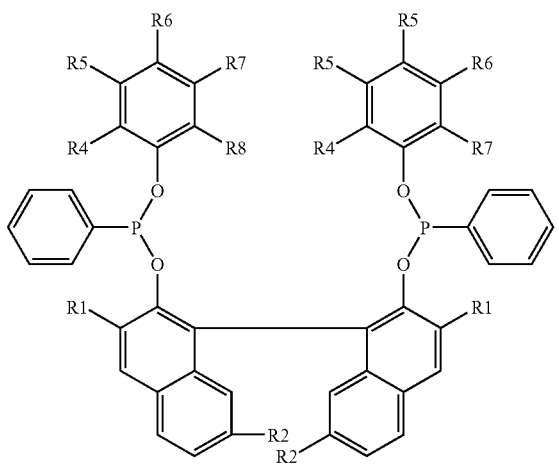

formula 2 where
  R1, R2 are each, independently of one another, hydrogen, an alkyl or alkylene group having from 1 to 8 carbon atoms or an alkoxy group having from 1 to 8 carbon atoms, with the proviso that R1 and R2 are not simultaneously H,
  R3 is H or methyl,
  R4 is t-butyl,
  R5, R6, R7, R8, R9 are each, independently of one another, H or an alkyl or alkylene group having from 1 to 8 carbon atoms.

2. A phosphonite I as claimed in claim 1 in which R1, R2 are selected independently from the group consisting of H, methyl, ethyl, n-propyl, i-propyl, n-butyl, s-butyl, i-butyl, t-butyl and methoxy.

3. A phosphonite I as claimed in claim 1 in which R1, R2 are selected independently from the group consisting of H, methyl, ethyl, n-propyl, i-propyl, t-butyl and methoxy.

4. A transition metal complex comprising a phosphonite I as claimed in claim 1 as ligand.

5. A transition metal complex as claimed in claim 4, wherein the transition metal used is nickel.

6. A process for preparing transition metal complexes as claimed in claim 4, which comprises reacting an elemental transition metal or a chemical compound containing a transition metal with a phosphonite I.

7. A catalyst comprising a transition metal complex as claimed in claim 4.

8. A process for the addition of hydrocyanic acid onto an olefinic double bond in the presence of a transition metal complex as claimed in claim 4 as catalyst.

9. A process as claimed in claim 8, wherein hydrocyanic acid is added onto butadiene to give a compound selected from the group consisting of 2-methyl-3-butenenitrile and 3-pentenenitrile.

10. A process for the isomerization of organic nitriles in the presence of a transition metal complex as claimed in claim 4 as catalyst.

11. A process as claimed in claim 10, wherein 2-methyl-3-butenenitrile is isomerized to 3-pentenenitrile.

12. A process as claimed in claim 8, wherein hydrocyanic acid is added onto 3-pentenenitrile, 4-pentenenitrile or a mixture thereof to give adiponitrile.

* * * * *